United States Patent [19]

Rescalli et al.

[11] Patent Number: 5,449,440
[45] Date of Patent: Sep. 12, 1995

[54] PROCESS FOR SEPARATING ALCOHOLS FROM MIXTURES OF ALCOHOLS, WATER AND OTHER COMPOUNDS

[75] Inventors: Carlo Rescalli; Flavio Cianci, both of San Donato Milanese, Italy

[73] Assignee: Snamprogetti S.p.A., Milan, Italy

[21] Appl. No.: 151,841

[22] Filed: Nov. 15, 1993

[30] Foreign Application Priority Data

Nov. 20, 1992 [IT] Italy ............... MI92A2658

[51] Int. Cl.⁶ ............................................. B01D 3/26
[52] U.S. Cl. .......................................... 203/20; 203/18; 203/78; 203/80; 203/99; 203/DIG. 13; 203/DIG. 19; 203/DIG. 23; 568/913
[58] Field of Search ............... 203/DIG. 13, DIG. 19, 203/DIG. 23, 20, 99, 78, 80, 18; 568/913, 916, 918

[56] References Cited

U.S. PATENT DOCUMENTS

| | | | |
|---|---|---|---|
| 3,293,154 | 12/1966 | Newton | 203/DIG. 23 |
| 3,293,435 | 3/1966 | Conpeiller et al. | 203/DIG. 23 |
| 3,391,064 | 7/1968 | Akell | 203/DIG. 23 |
| 3,434,937 | 3/1969 | Elliot et al. | 203/DIG. 23 |
| 4,210,495 | 7/1980 | Pinto | |
| 4,366,032 | 12/1982 | Mikitenko et al. | 203/DIG. 13 |
| 4,448,643 | 5/1984 | Lindner et al. | 203/DIG. 19 |
| 4,544,776 | 10/1985 | Osterburg et al. | 203/DIG. 19 |
| 4,645,570 | 2/1987 | Sridhar et al. | 203/DIG. 19 |
| 4,874,474 | 10/1989 | Rescalli et al. | 203/DIG. 23 |

FOREIGN PATENT DOCUMENTS

| | | |
|---|---|---|
| 0139981 | 5/1985 | European Pat. Off. . |
| 0306358 | 3/1989 | European Pat. Off. . |
| 0998857 | 7/1965 | United Kingdom ....... 203/DIG. 23 |
| 2203148 | 10/1988 | United Kingdom . |

Primary Examiner—Virginia Manoharan
Attorney, Agent, or Firm—Oblon, Spivak, McClelland, Maier & Neustadt

[57] ABSTRACT

From a mixture containing methanol, ethanol, n-propanol, isobutanol water and other high-boiling and low-boiling compounds, the claimed process enables three separate streams to be obtained, one an anhydrous stream of methanol or methanol and ethanol (I), one containing most of the n-propanol present in the feed mixture (II), and one containing most of the isobutanol present in the feed mixture (III), by using three fractionating columns.

12 Claims, 1 Drawing Sheet

PROCESS FOR SEPARATING ALCOHOLS FROM MIXTURES OF ALCOHOLS, WATER AND OTHER COMPOUNDS

BACKGROUND OF THE INVENTION

1. Field of the Invention

This invention relates to a process for obtaining streams of alcohols of different characteristics (methanol, ethanol, n-propanol, isobutanol) from mixtures thereof with water and other high-boiling or low-boiling organic compounds.

2. Discussion of the Background

Mixtures of methanol, ethanol, propanol, isobutanol and other compounds can be produced with greater or lesser quantities of water (by operating within suitable T and P ranges in the presence suitable catalysts) from synthesis gas obtained by partial oxidation of methane or naphtha, by methane steam reforming or by coal gasification.

Such mixtures can be used to obtain high-octane synthesis products and in particular methyl and ethyl ethers (MTBE and ETBE), these being products of ever increasing interest in the light of recent vehicle fuel legislation, both because of their octane characteristics and because of their oxygen content.

However the demand for MTBE in particular is increasingly difficult to cover by synthesis via the addition of methanol to the isobutene present in the $C_4$ streams from S.C. (steam cracking) and F.C.C. (fluid catalytic cracking) due to the poor availability of isobutene.

Alcohol mixtures obtained from CO and $H_2$ can also be used as sources of isobutene if the isobutanol contained in them is separated and dehydrated to olefin. In this manner such alcohol mixtures become a source of both the raw materials required for producing MTBE, ETBE or their mixtures, and hence become a strategic alternative to the classical production of these compounds by S.C. and F.C.C.

To make the synthesis of high-octane products such as MTBE and ETBE from alcohol mixtures obtained from CO and $H_2$ economically interesting, the available streams must be such as to allow certain restrictions to be satisfied, namely:

methanol can be used either alone or in mixture with ethanol, however in either case the water level must be very low; likewise in both cases the $C_3$ alcohol level must be minimized as it reacts with iso-olefins with unfavourable thermodynamics.

the propanol is preferably recycled to the reactor in which the alcohols are synthesized from CO and $H_2$ as this results in an increase in isobutanol production. If recycled to the alcohol synthesis reactor this stream can contain even considerable quantities of methanol and ethanol, the former being recovered as CO and $H_2$ and the latter being converted into isobutanol and hence into a higher value product.

The ethanol distribution between the stream withdrawn from the side take-off of the 1st column and the overhead stream from the 2nd column depends essentially on whether ethanol is to be produced in order to obtain ETBE in mixture with MTBE or whether isobutanol is to be produced in order to obtain more isobutene and hence more MTBE.

the isobutanol (and any other high-boiling products present) fed to dehydration to obtain isobutene must have negligible $C_2$ and $C_3$ light alcohol content to prevent production of light olefins which cannot be etherified by the catalyst system usually used for etherification to MTBE and ETBE and hence of no interest. However this stream can accept the presence of high-boiling products (oxygenated or not).

The separation cycle of the present invention provides a process which satisfies all the aforesaid restrictions. Separation from a mixture of propanol, water, isobutanol and other heavy compounds is difficult and costly, particularly because of the formation of homogeneous and heterogeneous binary azeotropes with the water.

In this respect, the difference in boiling point between the azeotropes of $nC_3OH$ and isobutanol with water is only about 3° C. (Azeotropic Data Vol. III No. 35, Advances in Chemistry series), the isobutanol azeotrope being heterogeneous. The difficulties of separating the two are further aggravated by hydraulic and mechanical problems inherent in columns with phase separation (the behaviour of any high-boiling compound towards water is very similar to that of isobutanol).

The current art would suggest separating the methanol as overhead in a first column, then the water by azeotropic distillation in the presence of a suitable entrainer additive (using two columns), and then the ethanol and propanol in a further two fractionating columns (the isobutanol remains as bottoms in the last column). This cycle is of extremely high capital and operating cost, due mainly to the water separation.

SUMMARY OF THE INVENTION

The process of the invention achieves all the objects for a substantially simpler plant (substantially only three fractionating columns, one of which is small), of considerably lower operating cost than the aforesaid cycle suggested by the current art.

DETAILED DESCRIPTION OF THE PREFERRED EMBODIMENTS

Figure 1:
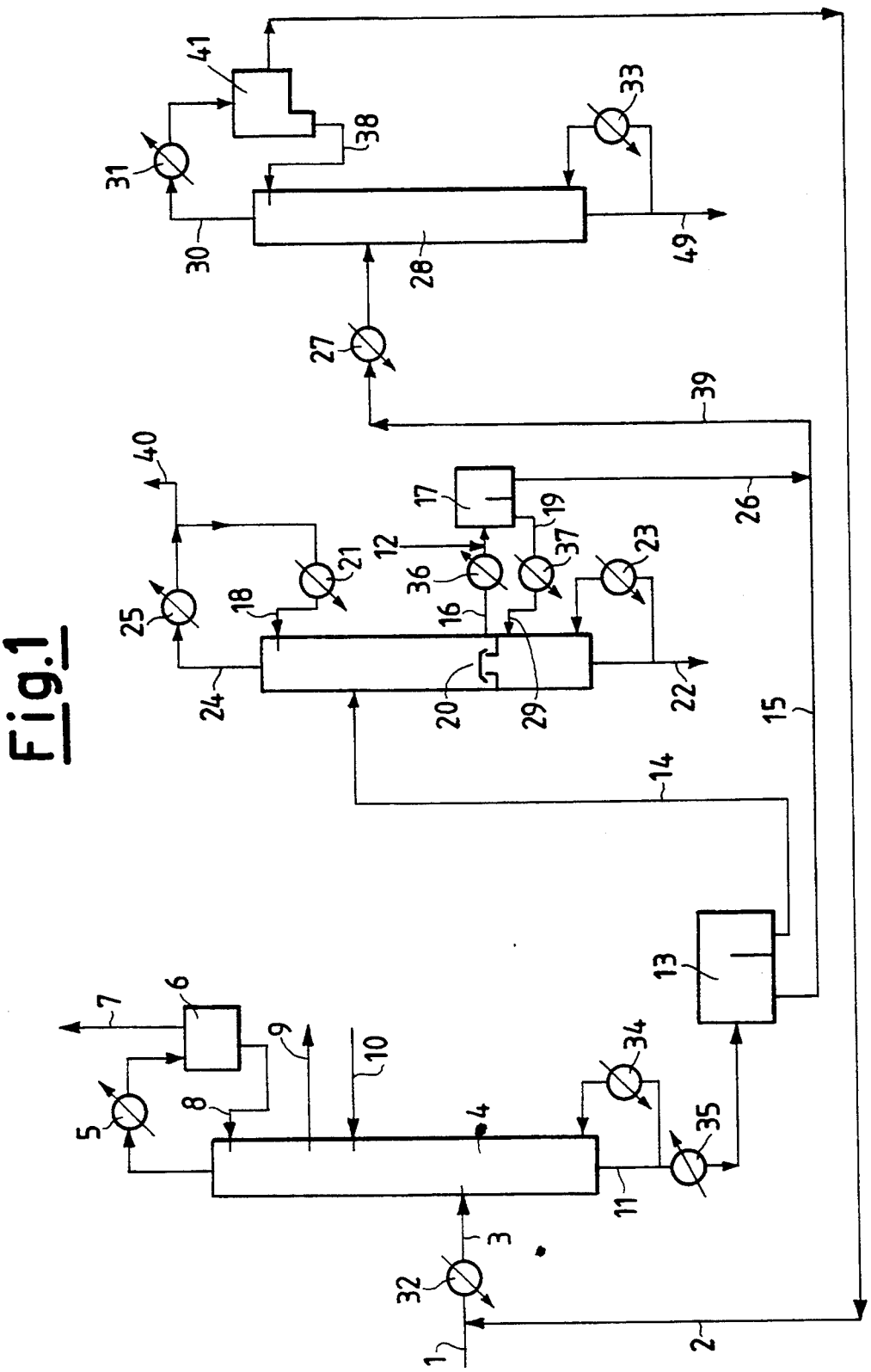
FIG. 1 is a scheme representing one embodiment of the process of the present invention.

The process for obtaining three separate streams, one an anhydrous stream consisting essentially of methanol or methanol and ethanol (I), one containing most of the n-propanol present in the feed mixture together with at least small quantities of methanol, ethanol, isobutanol and water (II), and one containing most of the isobutanol and the other high-boiling compounds contained in the feed mixture (III), from a mixture containing from 1 to 70 wt % of methanol and preferably from 5 to 30%, from 0.1 to 10 wt % of ethanol and preferably from 0.1 to 5%, from 0.1 to 20 wt % of n-propanol and preferably from 1 to 15%, from 2 to 80 wt % of isobutanol and preferably from 25 to 70%, and from 0.1 to 50 wt % of water and preferably from 1 to 30%, the remainder to 100 substantially consisting of other low-boiling and high-boiling organic compounds either of alcoholic type (such as isopropanol, n-butanol etc.) or not (oxygenated compounds such as ethers, esters, ketones, aldehydes, acids, heterocyclic compounds etc. and/or non-oxygenated compounds such as saturated, unsaturated, aromatic hydrocarbons etc.), is characterised by comprising the following steps:

feeding said mixture to a first fractionating column to discharge as overhead a stream containing essentially the inerts and the low-boiling compounds, withdrawing from a side point above the feed the anhydrous liquid stream (I) consisting essentially of methanol or methanol and ethanol, and obtaining from the bottom a liquid stream containing substantially all the n-propanol, the isobutanol, the water and the other high-boiling compounds, part of the methanol and part or all of the ethanol contained in the feed mixture;

feeding the stream from the bottom of the first fractionating column, or the organic phase possibly obtained by cold phase separation of this bottom stream, to a second fractionating column to obtain as overhead the stream (II) containing most of the n-propanol of the feed mixture, withdrawing from a side point below the feed point a liquid stream which, after cooling, is separated into two phases, namely an aqueous phase and an organic phase, this latter being recycled to a point immediately below said withdrawal point, and obtaining from the bottom the stream (III) (liquid or vapour phase) containing most of the isobutanol and high-boiling compounds of the feed mixture;

feeding the aqueous phase separated from the liquid stream withdrawn from the side take-off point of the second fractionating column, together possibly with the aqueous phase separated from the stream obtained from the bottom of the first fractionating column, to a third fractionating column, to recover as overhead the alcohols and the other organic compounds contained therein and discharging from the bottom a stream consisting essentially of water, the operating pressures of said columns and phase separators being chosen in the range of 30 to 500 Pascal absolute, and preferably between 100 and 300.

An antifoaming solution such as an aqueous silicone solution can be fed into the first fractionating column (preferably at a point immediately below the side withdrawal point of the stream (I), and/or into the second fractionating column (preferably into the liquid phase in the condenser).

The stream (III) is preferably used to obtain isobutene by dehydration in the presence of a suitable catalyst.

The stream (I) (the water content of which is always less than 1000 ppm by weight) withdrawn from a side point of the first column is used preferably for adding to the isobutene produced by dehydrating the isobutanol, and hence to produce MTBE or MTBE/ETBE mixtures, but can be partly recycled to the alcohol synthesis reactor or be used for other purposes (such as for solvent-grade methanol production if the ethanol is totally discharged from the bottom of the first column).

The stream (II) is preferably recycled to the reactor for synthesizing alcohols from CO and $H_2$, for converting the n-propanol to isobutanol with consequent upvaluing of the n-propanol. Even relatively high methanol, ethanol and isobutanol quantities can be permitted in said stream (II) because the recycling to the reactor enables them to be recovered. For the same reason (recycling to the reactor) the water content does not have to be as low as in stream (I).

Phase-separation of the liquid stream withdrawn from a side point of the second fractionating column allows removal of most of the water fed to the column, so that the n-propanol/isobutanol separation in the lower part of the column can be performed in the absence of water, resulting in a considerable increase in the separability of the system of the invention. This is well indicated by the fact that the boiling point of the two anhydrous compounds differs by 10° C. instead of the approximately 3° C. of the hydrated system. The absence of water also eliminates the mechanical problems associated with the phase separation of the liquid streams on the plates, so raising their efficiency.

The stream (III) is practically free of n-propanol, and can be used to generate isobutene (and other heavier olefins), for use together with the methanol or methanol plus ethanol stream (I) in producing MTBE or MTBE plus ETBE.

If the effluent from the alcohol synthesis reactor has a relatively high concentration of aldehyde, ketone or acid by-products, this stream can be advantageously hydrogenated before being fed to the separation cycle of the invention.

To totally eliminate traces of acid compounds, this stream or the stream discharged from the bottom of the first column (before any phase separation), or the stream withdrawn from the side take-off of the second column (before phase separation), or the organic phase discharged from the first phase separator (if present), can be fed through beds of basic ion exchange resins of various types (such as the type comprising $-N(R_i)$-$_3$—OH quaternary ammonium groups), or alternatively be treated with aqueous solutions of NaOH and/or other basic products such as carbonates, phosphates of alkaline or alkaline earth metals and/or other basic compounds of nitrogenated type, etc.

The cycle can easily allow the production of isobutanol at high purity (if required), even if the feed to the cycle contains high concentrations of high-boiling compounds. To achieve this it is necessary merely to feed the stream from the bottom of the second column to an auxiliary fractionating column. From the top of this latter column isobutanol can be obtained at a purity>95%, and can for example produce (by dehydration to isobutene followed by etherification) high-octane mixtures of higher MTBE content. The invention is described in detail hereinafter with reference to the scheme of FIG. 1, which represents a preferred but non-limiting embodiment of the invention.

After possible hydrogenation, not shown in the figure, the alcohol mixture from the synthesis reactor reaches the separation cycle via the line 1, and together with the recycled stream 2 is preheated in 32 and fed via 3 to the fractionating column 4. After partial condensation in 5, a gaseous stream 7 leaves the reflux vessel 6 and is vented to eliminate all the low-boiling compounds or compounds of similar behaviour by virtue of the formation of low-boiling azeotropes (ethers, hydrocarbons etc.). The liquid stream 8 discharged from the vessel 6 is returned to the top plate (after possible reheating in a heat exchanger, not shown). The anhydrous methanol or methanol plus ethanol stream 9 is withdrawn from a column plate above the feed plate. An antifoaming solution is fed through the line 10 immediately below the line 9.

The bottom stream 11 (free of methanol and ethanol) is discharged and, if the stream 1 is rich in water, undergoes phase separation in 13 after being cooled in 30.

This phase separator is however not essential to the operation of the cycle concerned. The organic phase 14 discharged from 13, or alternatively the stream 11 if the phase separator 13 is not provided, is fed to the second fractionating column 20.

The stream 24 discharged from the top and condensed in 25 is partly recycled to the alcohol synthesis reactor (line 40) and partly returned as reflux (line 18) after being preheated in 21. The stream 40 contains most of the propanol fed to the cycle, all the methanol and ethanol still present in 14 and a small quantity of isobutanol. In this recycled stream the presence of the water deriving from the water-ethanol, water-propanol and water-isobutanol azeotropes can be tolerated. The liquid stream 16 withdrawn from a plate below the feed is cooled in 36 and fed to the phase separator 17 which separates it into an aqueous phase 26 and an organic phase 19 (a water-saturated mixture consisting mainly of isobutanol and high-boiling compounds), which after preheating in 37 is recycled via the line 29 to the column 20 immediately below the plate from which the stream 16 was withdrawn. The aqueous phase 26, with a small isobutanol concentration, contains all the water fed to the separation cycle with the exception of that discharged from the top of 20 (line 40) and the small quantities present in the streams 7 and 9. This water withdrawal through the line 26 (via 17) enables the propanol-isobutanol separation in the lower part of 20 to be conducted in an anhydrous environment. This condition is much more favourable than the hydrated condition and enables a stream to be discharged without much difficulty from the bottom (line 22) containing most of the isobutanol fed to the cycle (together with the other high-boiling compounds present in the stream 14 plus a very small quantity of propanol).

An aqueous NaOH solution can be fed through the line 12 to neutralize any acid compounds present. The salts which form are removed via the line 26.

The stream 22 is fed to a suitable reactor for dehydration to isobutene (other olefins can derive from the heavy compounds present). This isobutene is then fed to an etherification reactor where, in the presence of a suitable catalyst and with the addition of the stream 9, it is converted into MTBE and ETBE (other ethers may also be generated from the other olefins produced from the heavy compounds).

The aqueous stream 26, together with the stream 15 (if the phase separator 13 is used), is fed via the line 39 to the heat exchanger 27 and then to the final separation column 28, from the bottom of which a stream 29 is discharged consisting only of water (with the possible presence of salts, if NaOH or other bases have been added via the line 12 or at other points of the cycle). This stream can be fed to a classical water treatment plant for final disposal. The overhead stream 30 is condensed in 31 and then partly fed as reflux via the line 38 (after possible reheating in a heat exchanger, not shown) and partly recycled to the cycle feed for recovering the isobutanol contained in the stream 39. The vessel 41 is designed to allow continuous total flowback of any aqueous phase present in it, so as to ensure that only an organic phase is recycled through the line 2.

An example is given to illustrate the significance of the present invention, but must not be considered as limitative of the invention itself.

EXAMPLE

The process follows the scheme of FIG. 1.

The first fractionating column 4 (stage glass plate column, $\phi=50$ mm, 80 plates in total, feed point 25th plate from the bottom, overhead pressure atmospheric, side withdrawal at the 70th plate from bottom) is fed at 55° C. with the stream 3 (sum of stream 1 (effluent from the alcohol synthesis reactor), and stream 2 (recycled from 28)), consisting of:

|  | Stream 1 g/h | Stream 2 g/h | Stream 3 g/h |
|---|---|---|---|
| low-boiling compounds | 9.0 | — | 9.0 |
| water | 76.4 | 1.8 | 78.2 |
| methanol | 185.4 | — | 185.4 |
| ethanol | 5.6 | — | 5.6 |
| n-propanol | 84.2 | 2.4 | 86.6 |
| isobutanol | 408.9 | 1.9 | 410.8 |
| high-boiling compounds | 230.5 | — | 230.5 |
| total | 1000.0 | 6.1 | 1006.1 |

A gaseous stream 7 of 10.0 g/h is discharged from the vessel 6 at 40° C. containing together with other organic components all the dimethylether present in the feed plus a small quantity of methanol (1.0 g/h). The liquid phase 8 in equilibrium is returned as reflux at a rate of 677.9 g/h.

The liquid stream withdrawn from the 70th plate (at 69° C.) comprises:

| water | $\leq 0.2$ g/h (<0.1 wt %) |
|---|---|
| methanol | 184.0 g/h |
| ethanol | 4.1 g/h |
| total | 188.3 g/h |

An aqueous solution containing 1 wt % of a silicone antifoaming agent (1.0 g/h—not considered in the mass balance) is fed onto the 65th plate.

The stream 11 is discharged from the bottom (at 102° C.) and is fed directly to the column 20 (plate column with the same characteristics as the preceding, operating at atmospheric pressure, with 70 plates in total, feed to 40th plate, side withdrawal from 35th plate).

The streams 40 and 18 are recycled from the column top (at 89°) to the alcohol synthesis reactor and to the column respectively, and consist of:

|  | (40) g/h | <—wt %—> | | (18) g/h |
|---|---|---|---|---|
| water | 35.2 | 23.9 | | 247.3 |
| methanol | 0.4 | 0.3 | | 3.0 |
| ethanol | 1.5 | 1.0 | | 10.3 |
| propanol | 82.4 | 56.6 | | 585.6 |
| isobutanol | 26.6 | 18.2 | | 188.3 |
| total | 145.9 | 100.0 | | 1034.5 |

The liquid phase 16 withdrawn (at 95° C.) from the 35th plate is cooled to 20° C. in 36 and phase-separated in 17. From here the aqueous stream 26 is discharged, it comprising:

| water | 43.0 g/h |
|---|---|
| propanol | 2.4 g/h |
| isobutanol | 1.9 g/h |
| total | 47.3 g/h |

The organic stream 29 is recycled after preheating to 90° C. in 37. The stream 22 is discharged from the bottom at about 120° C., it comprising:

| | |
|---|---|
| propanol | 1.8 g/h |
| isobutanol | 382.3 g/h |
| heavies | 230.5 g/h |
| total | 614.6 g/h |

The stream 26, preheated to 80° C. in 27, is fed to the column 28 (plate column of the same characteristics as the preceding, operating at atmospheric pressure, with a total of 25 plates and fed onto the 15th plate from the bottom).

The overhead stream 30 (at about 95° C.) is condensed in 31 and partly returned as reflux through line 38 (18.3 g/h) and partly recycled to the cycle feed via the line 2 (6.1 g/h). The bottom stream 29 (41.2 g/h) consists only of water and is eliminated.

We claim:

1. A process for separating a feed mixture of from 1 to 70 wt % methanol, from 0.1 to 10 wt % ethanol, from 0.1 to 20 wt % n-propanol, from 2 to 80 wt % isobutanol, from 0.1 to 50 wt % water, and the remainder to 100 wt % of low-boiling organic compounds and high-boiling organic compounds; comprising
   (a) feeding to a first fractionating column via a side inlet said feed mixture so as to discharge (i) from the top of said first column, a gaseous stream consisting essentially of a portion of said low boiling organic compounds; (ii) from a side outlet located at a point above said side inlet, an anhydrous liquid stream consisting essentially of a portion of said methanol, ethanol or a mixture thereof; and (iii) from the bottom of said column, a liquid stream consisting essentially of substantially all of said n-propanol, isobutanol, water and height-boiling compounds and a portion of said methanol, ethanol or mixture thereof;
   (b) feeding said liquid stream of (a) (III) into a second fractionating column through a first side inlet so as to discharge (i) from the top of said second column, a stream comprising a portion of said n-propanol and a portion of said methanol, ethanol, isopropanol and water; (ii) from a side outlet below said side inlet, a liquid stream which, after cooling, is separated into an aqueous and an organic phase, said organic phase being recycled to a second side inlet immediately below said side outlet; and (iii) from the bottom of said column, a liquid stream comprising a portion of said isobutanol and high-boiling compounds; and
   (c) feeding said aqueous phase of (b) (ii) to a third fractionating column so as to discharge (i) from the top of said column, an organic stream consisting essentially of methanol, ethanol, n-propanol, isobutanol and high-boiling compounds, which is recycled by being added to said feed mixture before the latter is fed to said first fractionating column and (ii) from the bottom of said first fractionating column and (ii) from the bottom of said column, a stream consisting essentially of water;
   wherein said fractionating columns are operated in the range of 30 to 500K Pascal absolute.

2. A process as claimed in claim 1, wherein the feed mixture contains:
   from 5 to 30 wt % of methanol,
   from 0.1 to 5 wt % of ethanol,
   from 1 to 15 wt % of non-propanol,
   from 25 to 70 wt % of isobutanol,
   from 1 to 30 wt % of water,
   the remainder to 100 wt % of low-boiling organic compounds and high-boiling organic organic compounds.

3. A process as claimed in claim 1, wherein said fractionating columns are operated in the range of from 100 to 300K Pascal absolute.

4. A process as claimed in claim 1, wherein an antifoaming solution is fed into the first fractionating column and/or the second fractionating column.

5. A process as claimed in claim 1, wherein an antifoaming solution is fed at a point immediately below the side outlet of the stream obtained in (a) (ii).

6. A process as claimed in claim 1, wherein an antifoaming solution is fed into said liquid phase obtained in (b) (ii).

7. A process as claimed in claim 1, wherein a solution of NaOH and/or basic compounds selected from the group consisting of carbonates, bicarbonates and phosphates of alkaline and alkaline earth metals, and/or basic nitrogenated compounds selected from the group consisting of amines and alkanolamines is added to the stream obtained in (a) (iii) or to the stream obtained in (b) (ii).

8. A process as claimed in claim 1, wherein the stream obtained in (b) (iii) is used to obtain isobutene by dehydration in the presence of a catalyst.

9. A process as claimed in claim 8, wherein the stream obtained in (a) (ii) is added to the isobutene obtained by dehydrating the isobutanol, to produce MTBE or MTBE and ETBE mixtures.

10. A process as claimed in claim 8, wherein part of the stream obtained in (a) (ii) is recycled to a reactor for synthesizing alcohols from CO and $H_2$.

11. A process as claimed in claim 1, wherein the stream obtained in (b) (i) is recycled to the reactor for synthesizing alcohols from CO and $H_2$.

12. The method of claim 1, wherein said liquid stream obtained in (a) (iii) is cold phase separated prior to (b) into an aqueous phase and an organic phase, and thereafter said organic stream is fed into said second fractionating column in (b) and said aqueous phase is combined with said aqueous phase obtained in (b) (ii) and fed into the third fractionating column in (c).

* * * * *